United States Patent [19]
Garey et al.

[11] Patent Number: 5,910,413
[45] Date of Patent: Jun. 8, 1999

[54] METHOD AND KIT FOR AMPLIFICATION, SEQUENCING AND TYPING OF CLASSICAL HLA CLASS I GENES

[75] Inventors: Caroline Elizabeth Garey, Toronto; James Leushner, North York, both of Canada

[73] Assignee: Visible Genetics, Inc., Toronto, Canada

[21] Appl. No.: 08/948,717

[22] Filed: Oct. 10, 1997

[51] Int. Cl.[6] .............................. C12Q 1/68; C07H 21/04
[52] U.S. Cl. ........................ 435/6; 435/810; 536/24.31; 536/24.33
[58] Field of Search .................... 435/6, 810; 536/24.33, 536/24.31

[56] References Cited

U.S. PATENT DOCUMENTS

| | | | |
|---|---|---|---|
| 5,424,184 | 6/1995 | Santamaria et al. | 435/6 |
| 5,451,512 | 9/1995 | Apple et al. | 435/91.2 |

FOREIGN PATENT DOCUMENTS

92/19771  11/1992  WIPO.

OTHER PUBLICATIONS

Johnstoan–Dow, et al. "A General Approach for Sequencing Based Typing of HLA–A" Poster Presentation, 1995 ASHI Meeting, Dallas, TX.

Blasczyk et al., "The Diversoty of the HLA Class I Introns Reflects the Ancestral Relationships of the Coding Regions", Abstracts of the 22nd Annual Meeting if The American Society of Histocompatability and Immunogenetics, No. 2.4–26 (1996).

Cereb et al., *Tissue Antigens* 45: 1–11 (1995).

Weiss et al., "Organization, Sequence and expression of the HLA–B27 Gene: Moelcular Approach to Analyze HLA and Disease Associations"*Immunobiol.* 170: 367–380 (1985).

Blascyzk et al., *Tissue Antigens* 47: 102–110 (1996).

Petersdorf et al., "A comprehensive approach for typing the alleles of the HLA–B locus by automated Sequencing" *Tissue Antigens* 46: 73–85 (1995).

Santamaria et al., *Human Immunology* 37: 39–50 (1993).

Saiki, et al., *Proc. Natl Acad. Sci.* (USA) 86: 6230–6234 (1989).

"HLA Class I SSP ARMS–PCR Typing Kit", Reference Manual (1995).

*Primary Examiner*—David Saunders
*Assistant Examiner*—F. Pierre VanderVegt
*Attorney, Agent, or Firm*—Oppedahl & Larson LLP

[57] ABSTRACT

Amplification primer and sequencing primer sites have been identified which permit sequence-based typing of each of the classical HLA genes in highly robust and consistent reactions without allelic dropout. To determine the DNA sequence, and thus the type of at least one exon of an HLA-A, HLA-B and HLA-C gene present in a sample, the sample is combined with an amplification reaction mixture containing the amplification primers and amplified to form an amplification product including exon 2 and exon 3 of the gene together in a single fragment. The amplification product is then combined with a sequencing reaction mixture containing one or more oligonucleotide sequencing primers which hybridize to a conserved regions the amplification product. The oligonucleotide sequencing primers between them are effective to produce sequencing fragments from all known alleles of exon 2 or exon 3 of the gene under suitable conditions to produce sequencing fragments. The sequencing fragments are then evaluated to determine the sequence of exon 2 or exon 3 of the gene in the sample.

9 Claims, 1 Drawing Sheet

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
       (A) LENGTH: 21
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
       (A) ORGANISM: human (ix) FEATURE:
       (D) OTHER INFORMATION: amplification primer for exons 2 and 3
           of HLA-A (xi) SEQUENCE DESCRIPTION: SEQ ID NO:1:

GGCCTCTGYG GGGAGAAGCA A                                              21

(2) INFORMATION FOR SEQ ID NO: 2:

(i) SEQUENCE CHARACTERISTICS:
       (A) LENGTH: 24
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
       (A) ORGANISM: human (ix) FEATURE:
       (D) OTHER INFORMATION: amplification primer for exons 2 and 3
           of HLA-A (xi) SEQUENCE DESCRIPTION: SEQ ID NO:2:

AGCAGGGCGG AACCTCAGAG TCAC                                           24

(2) INFORMATION FOR SEQ ID NO: 3:

(i) SEQUENCE CHARACTERISTICS:
       (A) LENGTH: 20
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: yes (v) FRAGMENT TYPE: internal -continued (vi) ORIGINAL SOURCE:
         (A) ORGANISM: human (ix) FEATURE:
         (D) OTHER INFORMATION: amplification primer for exons 2 and 3
             of HLA-B (xi) SEQUENCE DESCRIPTION: SEQ ID NO:3:

GGCGGGGCG CAGGACCTGA                                              20

(2) INFORMATION FOR SEQ ID NO: 4:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: amplification primer for exons 2 and 3
             of HLA-B (xi) SEQUENCE DESCRIPTION: SEQ ID NO:4:

CGGGGGCGCA GGACCCGG                                               18

(2) INFORMATION FOR SEQ ID NO: 5:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (D) OTHER INFORMATION: amplification primer for exons 2 and 3
             of HLA-B (xi) SEQUENCE DESCRIPTION: SEQ ID NO:5:

CCATCCCCGS CGACCTATAG G                                           21

(2) INFORMATION FOR SEQ ID NO: 6:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for exons 2 and 3
            of HLA-C (xi) SEQUENCE DESCRIPTION: SEQ ID NO:6:

AGGAGCGAGGKGC CCGCC                                                    18

(2) INFORMATION FOR SEQ ID NO: 7:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for exons 2 and 3
            of HLA-C (xi) SEQUENCE DESCRIPTION: SEQ ID NO:7:

GCTGATCCCA TTTTCCTCCC CTC                                              23

(2) INFORMATION FOR SEQ ID NO: 8:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: sequencing primers for exon 2 of
            classical HLA Class I genes (xi) SEQUENCE DESCRIPTION: SEQ ID NO:8:

GGTCGTGACC TYCGCCCC                                                    18

(2) INFORMATION FOR SEQ ID NO: 9:

(i) SEQUENCE CHARACTERISTICS:
        (A) LENGTH: 15
        (B) TYPE: nucleic acid
        (C) STRANDEDNESS: double
        (D) TOPOLOGY: linear

```
    (ii) MOLECULE TYPE: other nucleic acid (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: sequencing primers for exon 3 of
             classical HLA Class I genes (xi) SEQUENCE DESCRIPTION: SEQ ID NO:9:

CCCGGTTTCA TTTTC                                                        15

(2) INFORMATION FOR SEQ ID NO:10:

(i) SEQUENCE CHARACTERISTICS:
         (A) LENGTH: 21
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: sequencing primer for exon 2 of HLA-A (xi) SEQUENCE DESCRIPTION: SEQ ID NO:10:

TCCCACTCCA TGAGGTATTT C                                                 21

(2) INFORMATION FOR SEQ ID NO:11:

(i) SEQUENCE CHARACTERISTICS:
         (A) LENGTH: 18
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (D) OTHER INFORMATION: sequencing primer for exon 2 of HLA-A (xi) SEQUENCE DESCRIPTION: SEQ ID NO:11:

ATCTCGGACC CGGAGACT                                                     18

(2) INFORMATION FOR SEQ ID NO:12:

(i) SEQUENCE CHARACTERISTICS:
         (A) LENGTH: 22
         (B) TYPE: nucleic acid
         (C) STRANDEDNESS: double
```

(D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: sequencing primer for exon 3 of HLA-A (xi) SEQUENCE DESCRIPTION: SEQ ID NO:12:

GTTTCATTTT CAGTTTAGGC CA                                                22

(2) INFORMATION FOR SEQ ID NO:13:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (D) OTHER INFORMATION: sequencing primer for exon 3 of HLA-A (xi) SEQUENCE DESCRIPTION: SEQ ID NO:13:

GATATTCTAG TGTTGGTCCC A                                                 21

(2) INFORMATION FOR SEQ ID NO:14:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: sequencing primer for exon 2 of HLA-B (xi) SEQUENCE DESCRIPTION: SEQ ID NO:14:

TCCCACTCCA TGAGGTATTT C                                                 21

(2) INFORMATION FOR SEQ ID NO:15:

(i) SEQUENCE CHARACTERISTICS:
            (A) LENGTH: 18
            (B) TYPE: nucleic acid (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: sequencing primer for exon 2 of HLA-B (xi) SEQUENCE DESCRIPTION: SEQ ID NO:15:

ATCTCGGACC CGGAGACT                                                      18

(2) INFORMATION FOR SEQ ID NO:16:

(i) SEQUENCE CHARACTERISTICS:
        (A) LENGTH: 16
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: sequencing primer for exon 3 of HLA-B (xi) SEQUENCE DESCRIPTION: SEQ ID NO:16:

GGKCCAGGGT CTCACA                                                        16

(2) INFORMATION FOR SEQ ID NO:17:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: sequencing primer for exon 3 of HLA-B (xi) SEQUENCE DESCRIPTION: SEQ ID NO:17:

TCCCCACTGC CCCTGGTA                                                      18

(2) INFORMATION FOR SEQ ID NO:18:

(i) SEQUENCE CHARACTERISTICS:
        (A) LENGTH: 21

(B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: sequencing primer for exon 2 of HLA-C (xi) SEQUENCE DESCRIPTION: SEQ ID NO:18:

TCCCACTCCA TGAGGTATTT C                                              21

(2) INFORMATION FOR SEQ ID NO:19:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: sequencing primer for exon 2 of HLA-C (xi) SEQUENCE DESCRIPTION: SEQ ID NO:19:

GAGGAGGGGT CGTGACC                                                   17

(2) INFORMATION FOR SEQ ID NO:20:

(i) SEQUENCE CHARACTERISTICS:
        (A) LENGTH: 16
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: sequencing primer for exon 3 of HLA-C (xi) SEQUENCE DESCRIPTION: SEQ ID NO:20:

GGKCCAGGGT CTCACA                                                    16

(2) INFORMATION FOR SEQ ID NO:21:

(i) SEQUENCE CHARACTERISTICS:

```
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: sequencing primer for exon 3 of HLA-C (xi) SEQUENCE DESCRIPTION: SEQ ID NO:21:

TCCCCACTGC CCCTGGTA                                                        18
```

METHOD AND KIT FOR AMPLIFICATION, SEQUENCING AND TYPING OF CLASSICAL HLA CLASS I GENES

BACKGROUND OF THE INVENTION

This application relates to a method and kit for high-resolution, DNA-based typing of the three classical HLA Class I genes, namely the HLA-A, HLA-B, and HLA-C loci, in a patient sample.

The HLA Class I genes comprise the three classical genes encoding the major transplantation antigens HLA-A, HLA-B, and HLA-C and seven other Class I genes of which HLA-E, HLA-F and HLA-G are probably functional genes and HLA-H, HLA-I, HLA-K and HLA-L are pseudogenes. All classical Class I genes have a similar structure: Exon 1 (73 bp)—Intron 1 (130 bp)—Exon 2 (270 bp)—Intron (272 bp)—Exon 3 (276 bp)—Intron 3 (588 bp). The classical Class I genes are highly polymorphic. As of 1996, at least 82 alleles of HLA-A, 186 of HLA-B and 42 of HLA-C had been identified.

Methods for determining HLA-A, HLA-B, and HLA-C alleles in a patient sample have been heavily investigated because of the functional importance of these genes in transplant tissue matching and autoimmune diseases. Serological tests including the complement-dependent cytotoxicity assay (see Terasaki and McClelland, Nature, 204:998, (1964)) providing low resolution identification of HLA type have been most commonly applied to date. Unfortunately, such low resolution tests cannot detect and distinguish all functionally significant transplant antigens (Anasetti et al. Hum. Immunol., 29:70 (1990)).

High resolution tests are more desirable because they lead to improved tissue matching and reduced transplant rejection. Current methods of high resolution typing include using Sequence-Specific Oligonucleotide Probes (SSOP). The SSOP technique is well illustrated in U.S. Pat. No. 5,451,512 assigned to Hoffman-La Roche, Inc. Using a reverse dot blot format, HLA-A probes are immobilized on a membrane, and the labeled target (patient sample) DNA is hybridized to the membrane-bound probe as described in Saiki et al., 1989, Proc. Natl. Acad. Sci. 86:6230–6234. The sites of hybridization are detected, and HLA-A type can be deduced. This method does not involve direct DNA sequencing.

Another high resolution test is the Amplification Refractory Mutation System (ARMS) (see "HLA Class I SSP ARMS-PCR typing kit" Reference manual, June 1995 edition. Imperial Cancer Research Fund). Since primers which do not match target nucleic acid are not amplified under stringent hybridization conditions, the use of primers with specifically designed 3'-ends for amplification allows the allelic composition to be determined on the basis of which ARMS primers fail to amplify, and which ones are successful. This method does not involve direct DNA sequencing.

A direct DNA sequencing method for HLA Class I typing has been proposed by Santamaria et al ("HLA Class I Sequence-Based Typing" Hum. Immunol. 37, 39–50 (1993); WO 9219771; U.S. Pat. No. 5,424,184). This method has identified oligonucleotide primers for amplification and sequencing of the classical Class I genes. The method suffers because it focuses on cDNA (exon) sequences which, because of the sequence diversity, offer a very limited selection of conserved primer hybridization sites. Further, the sites disclosed were determined before the recent discovery of dozens of more alleles that now need to be considered in identifying HLA type. In addition, because the Santamaria sequencing primers hybridize within an exon, they do not provide information for DNA sequence upstream of the primer which is potentially decisive for distinguishing among alleles.

Intron sequences, as disclosed in the instant patent application, provide the preferred hybridization sites for amplification and sequencing primers for the HLA-A, HLA-B and HLA-C genes. Intron sequences for an HLA Class I gene were disclosed at least as early as 1985. (Weiss et al Immunobiol 170:367–380, (1985)). Due to the substantial diversity, and the difficulties in sequencing, few intron sequences have been published subsequently. A report of Blasczyk and Wehling (in Abstracts of The American Society for Histocompatability and Immunogenetics 22nd Annual Meeting, Oct. 11–15, 1996) states that intron sequences have been determined in 48 well-defined cell lines and 195 PCR-typed clinical samples.

Cereb et al. (Tissue Antigens 1995: 45:1–11), undertook the identification of intron sequences useful for locus-specific amplification primer sets for all Class I genes. Amplified fragments were characterized by SSOP and no direct sequencing of the amplified fragments was performed.

Blasczyk et al. have disclosed primers for use in amplification of the HLA-A locus in preparation for sequence-based typing of a sample. *Tissue Antigens* 47: 102–110 (1996). Twenty-one different primer mixes having different serologically defined specificities were identified for amplification of the second and third exons of the HLA-A gene. The resulting amplification products were then analyzed by sequencing.

Johnston-Dow et al (Poster Presentation: 1995 ASHI Meeting, Dallas, Tex.) presented a system for direct sequence determination of HLA-A wherein degenerate exon-based primers were used to amplify exons 1 to 5 of the genomic HLA-A DNA sequence. Sequencing of the amplified fragment was obtained using degenerate primers which hybridize to intron regions flanking exons 2 and 3.

Direct sequencing of HLA-B alleles from an amplified genomic DNA fragment was performed by Petersdorf and Hansen. (Tissue Antigens 1995 46: 73–85). A total of five primer sets (ten different primers) with different allelic specificities were used to amplify genomic material, and the amplification products were then sequenced.

Notwithstanding the various efforts which have been made to develop effective methods for typing HLA genes, none of the methods previously disclosed actually provides a test which will permit rapid typing of HLA alleles using a minimum number of reagents in a manner which is reproducible and which, in ordinary use, actually achieves typing of all allelic variants. Thus, for example, certain primers may theoretically be capable of achieving amplification and subsequent sequencing of all allelic variants of one of the classical HLA genes, yet in practice reactions with these primers are found to suffer from dropouts which preclude the specific detection of some alleles. There remains, therefore, a need for a method and kit which obtain direct high-resolution sequence information for the HLA-A, HLA-B and/or HLA-C genes using a minimum of oligonucleotide primers for all alleles of the gene analyzed.

It is an object of the present invention to provide a method and kit for direct sequencing of the HLA-A, HLA-B, and/or HLA-C alleles comprising a minimum number of oligonucleotides which hybridize to intron regions of these genes and which between them can amplify all alleles of these genes.

It is a further object of the present invention to provide a method and kit for direct sequencing of the HLA-A, HLA-B, HLA-C alleles using a minimum number of oligonucleotides which hybridize to intron regions of these genes and which between them can sequence all alleles of these genes.

SUMMARY OF THE INVENTION

We have now identified preferred amplification and sequencing primer sites which permit highly robust and consistent amplification and sequence-based typing of exons 2 and 3 of each of the classical HLA genes using one amplification reaction and one 3'- and/or one 5'-sequencing reaction per locus. Thus, in accordance with the invention, there is provided a method for determining the allelic type of an HLA-A, HLA-B or HLA-C gene present in a sample comprising the steps of combining the sample with an amplification reaction mixture comprising a mixture of amplification primers selected from the among primers having the sequences given by Sequence ID Nos 1 and 2; Seq. ID Nos 3, 4 and 5; or Seq ID Nos. 6 and 7 and cycling the resulting mixture to produce an amplification product;

combining the amplification product with a sequencing reaction mixture comprising one or more oligonucleotide sequencing primers which hybridize to conserved regions of the amplification product, wherein the oligonucleotide sequencing primers between them are effective to produce sequencing fragments from all known alleles of exon 2 or exon 3 of the gene under suitable conditions to produce sequencing fragments;

evaluating the sequencing fragments to determine the sequence of at least a portion of exon 2 or exon 3 of the gene in the sample; and comparing the determined sequence with a standard sequence for known alleles to determine the allelic type of the gene in the sample. Sequencing is preferably performed using sequencing primers having the sequences given by Sequence ID Nos. 8–21. The amplification and sequencing primers may be packaged into a kit for easy distribution and test performance.

DETAILED DESCRIPTION OF THE INVENTION

Figure 1:
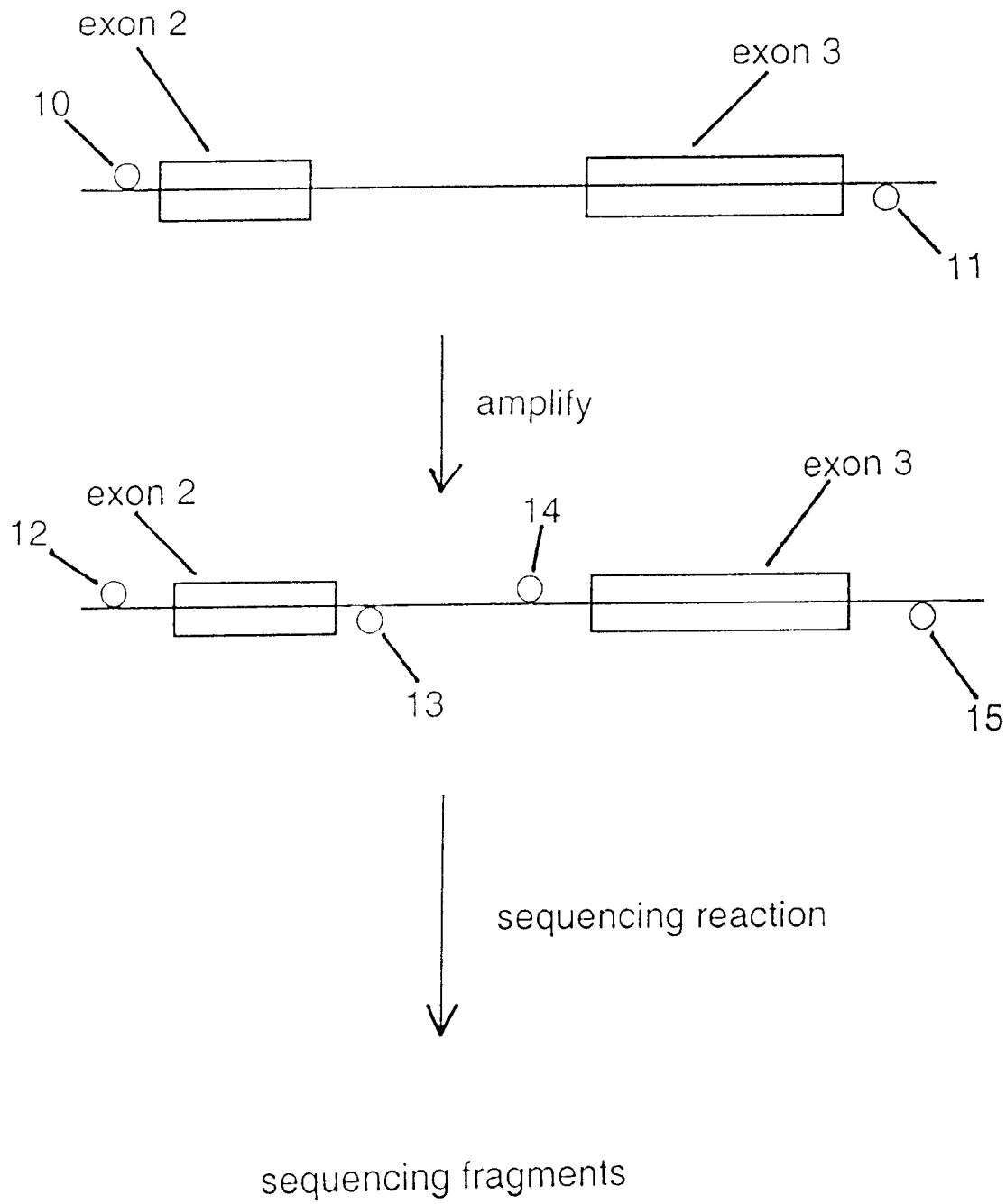
FIG. 1 shows the method of the invention schematically.

Virtually all the alleles of the classical HLA Class I genes (HLA-A, HLA-B and HLA-C) can be distinguished on the basis of exon 2 and 3 alone. The present invention takes advantage of this and provides a method and kit for DNA amplification and sequencing of an approximately 900 bp DNA fragment containing exons 2 and 3 of HLA-A, HLA-B and/or HLA-C by using primers which hybridize to targets in introns flanking these exons. These targets are highly specific to the locus in question and highly conserved among all alleles of the locus. The primers do not significantly co-amplify any pseudogenes or other Class I loci.

While the terminology used in this application is standard within the art, the following definitions of certain terms are provided to assure clarity.

1. "Allele" refers to a specific version of a nucleotide sequence at a polymorphic genetic locus.
2. "Amplification" refers to any form of preferential increase in the amount of one region of polynucleotide in a sample. Amplification is preferably performed using polymerase chain reaction (PCR) amplification as described in U.S. Pat. No. 4,436,202. This technique is well known in the art and thus will not be described in general terms but only through the specific example.
3. "Gene" or "Genetic locus" means a specific nucleotide sequence within a given genome.
4. The "location" or "position" of a nucleotide in a genetic locus means the number assigned to the nucleotide in the gene, generally taken from the cDNA sequence or the genomic sequence of the gene.
5. "Oligonucleotide primers" are short polynucleotides generally having a length of 10 to 40 bases which specifically hybridize with a defined site in a target polynucleotide.
6. "Polymorphism" means the variability found within a population at a genetic locus.
7. "Polymorphic site" means a given nucleotide location in a genetic locus which is variable within a population.
8. "Sequencing" refers to the process of determining the identity of nucleotide bases at each position along the length of a polynucleotide. Preferred sequencing methods include the chain termination technique first described by Sanger et al. and the variations thereon which have been subsequently developed. "Complete sequencing" refers to the determination of all four bases for a given polynucleotide. "Single-base sequencing" refers to determining the locations or positions of one type of nucleotide base within the polynucleotide, as described in U.S. patent application Ser. No. 08/577,858 filed Dec. 22, 1995, which is incorporated herein by reference.
9. The nucleotides Adenine, Cytosine, Guanine and Thymine are sometimes represented by their designations of A, C, G or T, respectively. Deoxynucleotide triphosphates are referred to collectively as dNTPs, and individually as dATP, dCTP, dGTP and dTTP. Chain-terminating dideoxynucleotide triphosphates are referred to collectively as ddNTPs, and individually as ddATP, ddCTP, ddGTP and ddTTP.

The basic format of the amplification and sequencing steps of the invention are outlined schematically in FIG. 1. FIG. 1 shows exons 2 and 3 of the HLA-A gene as they exist in genomic DNA together with intron sequences. Amplification primers 10 and 11 are used to amplify the approximately 900 bp sequence. The sequence of exon 2 may be determined using either or both of the primers 12 (sense strand) and 13 (anti-sense strand). The sequence of exon 3 may be determined using either or both of the primers 14 (sense strand) and 15 (anti-sense strand).

The crucial factor to the success of the method of the invention is the selection of primers for use in the amplification step. As a matter of first principle, amplification primers might be reasonably selected to hybridize with highly conserved hybridization sites in introns 1 and 3 of each of the classical HLA Class I genes that have been identified. Selected primers should also not hybridize with other sites on the classical HLA Class I genes (which could lead to amplification products of multiple lengths), and should not amplify any of the non-classical HLA Class I genes or any other gene found in tissue samples tested. Testing done in the development of the primers of the invention has established, however, that these criteria are not enough to ensure a successful analytical result. In particular, it has been observed that very small difference in primer sequences can lead to substantial differences in performance of the amplification reaction.

For example, in the case of HLA-A, amplification with a forward primer hybridizing with intron 1:25–46, and a reverse primer hybridizing with intron 3: 25–47 was found to be subject to allelic dropout of groups A24, A1 and A11 because the primers contained bases that were not conserved in the groups. Shifting to a different reverse primer (Seq. ID. No. 2) overcame this problem. Similarly, in the case of HLA-B, use of a forward primer hybridizing to intron 1: 36–37 produced difficulties in typing due to allelic dropouts of many groups. Using a combination of two forward primers hybridizing to intron 1: 57–76 and intron 1: 59–76 (Seq. ID Nos. 3 and 4) significantly reduces the drop out rate. Further improvements were obtained (eliminating dropout of B15 and B60 alleles) by moving the starting point of the reverse primer over 5 bases. (Seq. ID No. 5).

Other problems besides allelic dropout may also be encountered requiring selection of other primers, even though the precise reason for the experimental problem may not be apparent. This was observed when amplifying the HLA-C gene using a locus-specific forward primer hybridizing to intron 1: 42–61. This primer gave inconsistent PCR results, often failing despite several optimization attempts. Moving the primer over by three bases (Seq. ID No. 6) substantially improved the robustness of the PCR reaction. A further improvement was obtained when an early primer version hybridizing with intron 3:65–76 was shifted by a single base (Seq. ID No. 7) to eliminate dropout of 0702 alleles.

The amplification primer sets for the A, B and C loci can be used individually, that is the primers which are specific for the A locus can be used in one reaction while the primers specific for the B and C loci are used in two other, separate reactions. Alternatively, because the primers are truly locus-specific, all of the primers can be combined in a single reaction, to produce an amplification product mixture that contains HLA-A, HLA-B and HLA-C amplicons.

After the amplification reaction is completed, the amplified product is further evaluated by sequencing. The sequencing process can be a conventional four base sequencing procedure, in which the positions of each of the four bases is explicitly determined. Alternatively, single-base sequencing may be used to determine the positions of one base, or of two bases by doing a both forward and backward sequences simultaneously for a single base type, where the positions of one or two bases are sufficient to provide typing information. Again, the most important factor to the successful sequence determination is the selection of the sequencing primers.

The amplification primers (Seq. ID Nos. 1–7) can be used as sequencing primers to sequence the adjacent exon in one direction. Use of these primers generally sequences more material than is necessary for determination of the HLA type of the amplified product, however. Furthermore, the amplification primers cannot be used for sequencing of both strands. Thus it is preferred to use sequencing primers which more closely flank exon 2 or exon 3, yet which still hybridize with highly conserved regions of the gene such that a minimum number of sequencing primers can be used for evaluation of all alleles. Specific preferred sequencing primers which meet these criteria are given by Seq. ID. Nos. 8 and 9, which are universal primers which can be used for sequencing of HLA-A, HLA-B and HLA-C, and locus specific sequencing primers 10 through 21. As in the case of the amplification primers, small changes in the nature of the primer can result in significant changes in sequencing efficiency.

For example, for 5'-sequencing of exon 2 of HLA-A amplicons, initial efforts using an amplification primer hybridizing with intron 1:79–96 resulted in allelic dropout in groups A3, A25, A66, A28 and A26. Changing to a primer located just within exon 2 (Seq. ID No. 10) eliminated these dropouts without introducing other problems. Similarly, in the case of 5'-sequencing for exon 2 of the HLA-B locus, lengthening a primer spanning exon 2:2–19 by three bases and increasing the annealing temperature to 55° C. gave substantial improvement in the consistency of the sequencing fragment generated.

The 3'-sequencing primer for exon 3 of the HLA-B locus was also improved from an original primer employed (Intron 3:8–25) by shifting the primer 6 bases. (Seq. ID No. 17). This shift eliminated allelic dropout in groups B15, B35, B37, B42, B57, B60 and B61.

The remaining sequencing primers set forth in the example below have each been optimized to provide highly robust and consistent sequencing reactions using the specified chemistry. This level of performance is required if sequencing is to be used as a routine tool for HLA typing.

The sequencing primers used in the invention are preferably labeled with a detectable label, such as a fluorescent label, to permit ready detection of the sequencing fragments produced. If analysis is to be performed on a multi-dye instrument which is capable of differentiating between primers labeled with different fluorescent labels, the 3' and 5' -sequencing primers may be labeled differently, with spectroscopically distinguishable labels, to permit the simultaneous sequencing of both strands of the DNA. See, Wiemann et al., "Simultaneous On-Line DNA Sequencing on Both Strands with Two Fluorescent Dyes", *Anal. Biochem* 224: 117–121 (1995), which is incorporated herein by reference.

As an alternative to the use of labeled primers, dye-labeled chain terminators may be employed to produce detectable sequencing products.

The specificity of the amplification primers and the sequencing primers (other than the universal primers) makes it possible to significantly reduce the number of vessels required for typing of the classical HLA Class I genes and to increase the instrumental throughput. In particular, as noted above, all three of the classical loci can be amplified in a single reaction mixture using the locus-specific amplification primers. This mixed amplification product can then be combined with a sequencing reaction mixture containing distinctive locus-specific sequencing primers.

The preferred primers used in practicing the method of the invention are suitably packaged in kit form to facilitate distribution and performance of the tests. One such kit is a kit for amplification of the highly polymorphic portions of exons 2 and 3 of a classical HLA Class I gene comprising, in packaged combination, at least one set of amplification primers selected from the among the following primer sets:

Seq ID Nos 1 and 2;
Seq. ID Nos 3, 4 and 5; and
Seq ID Nos 6 and 7.

The kit may include primers for just one of the HLA loci or for a combination or two loci or for all three loci. The primers for any one locus may be packaged individually (e.g., one container with Seq. ID No. 1 and another container with Seq. ID No. 2), or as a mixture (Seq. ID Nos. 1 and 2 in the same container). The primers for the several loci may also be all provided in one mixture.

A second type of kit in accordance with the invention is a kit for sequencing of a highly polymorphic portion of exon 2 or 3 of a classical HLA Class I gene comprising, in packaged combination, at least one set of amplification primers for producing an amplification product from a classical HLA Class I gene, said set being selected from the among the following primer sets:

Seq ID Nos 1 and 2;

Seq. ID Nos 3, 4 and 5; and

Seq ID Nos 6 and 7; and at least one sequencing primer having a sequence that hybridizes to the amplification product under suitable conditions to produce sequencing fragments. Preferred sequencing primers are those having the sequences given by Seq ID Nos. 8–21. As noted above, the sequencing primers are preferably labeled with a detectable label such as a fluorescent label.

Either type of kit may also include additional reagents necessary for performing the amplification and/or sequencing reactions, including polymerase enzymes, dNTPs, ddNTPs, and appropriate buffers. These additional reagents are packaged separately or in combination as appropriate for the reaction to be performed.

A specific, highly robust method of high-resolution typing of HLA-A, HLA-B and HLA-C is detailed in example 1 below, which is set out to exemplify the method of the invention and not to limit the scope of it.

EXAMPLE 1

Determination of the classical HLA Class I genes (comprising the loci HLA-A; HLA-B; and HLA-C) in a patient sample may be achieved as follows.

Genomic DNA is prepared from the patient sample according to standard methods using detergent and proteinase K (Current Protocols in Molecular Biology, Eds. Ausubel, F. M. et al, (John Wiley & Sons; 1995)). An alternative method for extracting DNA from blood by salt precipitation is provided in the Puregene DNA Isolation Kit (Gentra Systems, Inc., Minneapolis).

A DNA fragment containing Exons 2 and 3 of each locus is first amplified in a standard PCR reaction. As indicated in FIGS. 1, 2 & 3, the amplification primers are selected to hybridize to intron regions flanking Exons 2 and 3 and conserved among all alleles of the locus.

The PCR reaction mixture consists of

|  |  | ul |
|---|---|---|
| $MgCl_2$ | 25 mM | 1.5 |
| deazadNTPs | 2.5 mM | 2.0 |
| DMSO | 100% | 2.5 |
| 10 × PCR Buffer* |  | 2.5 |
| $(NH_4)_2SO_4$ | 166 mM | 2.5 |
| $H_2O$ |  | 7.75 |

*1 × PCR Buffer comprises 10 mM Tris-HCl pH 8.3, 50 mM KCl.

The PCR reaction mixture is aliquoted into three tubes (one for each locus). One mixture of locus specific amplification primers is added to each tube (1 μL of 10 μM primer mixture containing equimolar amounts of forward and reverse primer). The locus-specific mixtures have the following compositions:

|  | Location |  |
|---|---|---|
| HLA-A Locus Specific Amplification Primers | | |
| Forward | | |
| GGCCTCTGYGGGGAGAAGCAA | Intron 1:25–46 | [Seq ID No. 1] |
| Reverse | | |
| AGCAGGGCGGAACCTCAGAGTCAC | Intron 3:160–136 | [Seq. ID No. 2] |
| HLA-B Locus Specific Amplification Primers | | |
| Forward | | |
| GGCGGGGGCGCAGGACCTGA | Intron 1:57–76 | [Seq ID No. 3] |
| CGGGGGCGCAGGACCCGG | Intron 1:59–76 | [Seq ID No. 4] |
| Reverse | | |
| CCATCCCCGGCGACCTATAGG | Intron 3:51–3 | [Seq ID No. 5] |

The two forward primers are used as an equimolar mixture.

| HLA-C Locus Specific Amplification Primers | | |
|---|---|---|
| Forward | | |
| AGCGAGGKGCCCGCCCGG | Intron 1:42–59 | [Seq ID No. 6] |
| Reverse | | |
| GCTGATCCCATTTTCCTCCCCTC | Intron 3:88–66 | [Seq ID No. 7] |

100–250 ng of patient sample DNA is added to each tube, along with 2.5 units of Taq Polymerase (Amersham International plc). The samples are mixed well and thermal cycled in a Robo-Cycler 9600 (Perkin-Elmer, Inc.) according to the following schedule:

94° C. for 5 minutes then 35 cycles of

94° C. for 30 sec

63° C. for 30 sec

72° C. for 60 sec followed by

72° C. for 5 minutes.

The reaction tube is then cooled on ice until required for the sequencing reactions. If desired, an aliquot of the amplified fragment can be observed on an agarose gel with ethidium bromide stain. Each fragment should appear as an approximately 900 bp band.

The order of sequencing reactions may be selected by the operator. Each exon of each locus may be sequenced on the sense strand or anti-sense strand. A preferred method is to obtain sequence from the sense strand (5' primer) from each exon. If the results contain ambiguities, then the amplicon is re-sequenced using the anti-sense strand (3' primer) for the same exon. The availability of both sequencing primers provides redundancy to ensure robust results.

The sequencing reaction mixture is prepared as follows:

|  | ul | Amount |
|---|---|---|
| PCR Amplicon | 4.5 | 30–100 ng |
| 100% DMSO | 3.5 | 10% |
| Sequencing Primer(s) | 2.5 | 9 pmol |
| Sequencing Buffer | 2.5 |  |
| Sequencing Polymerase | 3.0 | 8 U |
| $H_2O$ | 6.0 |  |
| final | 22.0 |  |

The sequencing buffer used is compatible with the enzyme used. For example, when THERMOSEQUENASE™ is used as the sequencing polymerase, 10× THERMOSEQUENASE™ Buffer consisting of 260 mM Tris-HCl (pH 9.5), 65 mM MgCl$_2$ is suitable. Other sequencing polymerase enzymes, such as TaqFS may be used with their own preferred buffer.

The sequencing primer selected may be a single oligonucleotide species, or, in the case of exon 3 of HLA-C, it may be an equimolar mixture of 2 or more oligonucleotide species. Mixtures of oligonucleotides are selected such that between them they will effectively prime the sequencing reactions for all alleles of the locus at the same site. Suitable sequencing primers are as follows:

| | Location | |
|---|---|---|
| Universal Primers for HLA-A, HLA-B and HLA-C | | |
| Exon 2 3' Sequencing GGTCGTGACCTYCGCCCC | Intron 2:35-18 | [Seq ID No. 8] |
| Exon 3 5' Sequencing CCCGGTTTCATTTTC | Intron 2:165-179 | [Seq ID No. 9] |
| Locus Specific Primers | | |
| HLA-A Sequencing Primers | | |
| EXON 2 | | |
| 5' SEQUENCING TCCCACTCCATGGAGGTTTTC | Exon 2:3-23 | [Seq ID No. 10] |
| 3' SEQUENCING ATCTCGGACCCGGAGACT | Intron 2:78-48 | [Seq ID No. 11] |
| EXON 3 | | |
| 5' SEQUENCING GTTTCATTTTCAGTTTAGGCCA | Intron 2:168-190 | [Seq ID No. 12] |
| 3' SEQUENCING GATATTCTAGTGTTGGTCCCA | Intron 3:78-98 | [Seq ID No. 13] |
| HLA-B Sequencing Primers | | |
| EXON 2 | | |
| 5' SEQUENCING TCCCACTCCATGAGGTATTTC | exon 2:2-19 | [Seq ID No. 14] |
| 3' SEQUENCING ATCTCGGACCCGGAGACT | Intron 2:78-98 | [Seq ID No. 15] |
| EXON 3 | | |
| 5' SEQUENCING GGKCCAGGGTCTCACA | Intron 2:258-Exon 3:9 | [Seq ID No. 16] |
| 3' SEQUENCING TCCCCACTGCCCCTGGTA | Intron 3:2-19 | [Seq ID No. 17] |
| HLA-C Sequencing Primers | | |
| EXON 2 | | |
| 5' SEQUENCING TCCCACTCCATGAGGTATTTC | Exon 2:3-23 | [Seq ID No. 18] |
| 3' SEQUENCING GAGGAGGGGTCGTGACC | Intron 2:25-41 | [Seq ID No. 19] |
| EXON 3 | | |
| 5' SEQUENCING GGKCCAGGGTCTCACA | Intron 2:258-Exon 3:9 | [Seq ID No. 20] |
| 3' SEQUENCING TCCCCACTGCCCCTGGTA | Intron 3:2-19 | [Seq ID No. 21] |

The sequencing primers are labeled on the 5' end with a detectable label, using phosphoramidite or NHS/dye ester techniques well known in the art. The label selected depends on the detection instrument employed. The label for use with an OPENGENE™ System (Visible Genetics Inc., Toronto, ON) is the fluorophore Cy5.5 (Amersham Life Sciences, Cleveland Ohio). Fluorescein isothiocyanate may be used for detection with the ALF Automated Sequencer (Pharmacia, Piscataway N.J.). Several labels may be employed in combination if a multi-dye instrument is employed.

5 μl of the sequencing primer mixture is added to each of 4 tubes containing 3 μl if 750 μM dNTPs (dATP, dCTP, dGTP and dTTP) and 7.5 μM of one ddNTP (ddATP, ddCTP, ddGTP or ddTTP). The sequencing reaction mixture is thermal cycled in a Robo-Cycler 9600 (Perkin Elmer Inc.) as follows:

94° C. for 30 sec then 35 cycles of

94° C. for 30 sec

55° C. for 30 sec

70° C. for 60 sec

At completion the samples are stored at 4° C. until ready for loading on an electrophoresis gel for sequence analysis.

For detection of reaction products, the sample is mixed with an equal volume of loading buffer (5% ficoll plus a coloured dye). 1.5 ul of these samples are loaded per lane of a MICROCEL™ electrophoresis cassette loaded in a MICROGENE BLASTER™ automated DNA sequencer (Visible Genetics Inc., Toronto). The sample is electrophoresed and the separated DNA bands detected.

Results are suitably analyzed and displayed with GENEOBJECTS™ software (Visible Genetics Inc, Toronto). The sequence of bases is determined, and the HLA allele to which the sequence corresponds is identified. This process is performed for each locus (HLA-A, HLA-B, HLA-C) and the results are reported to the patient file.

In rare cases, patients are homozygous for one allele at each locus. These cases are relatively easy to determine, even without software. For example a homozygotic sequence of HLA-A can only be one of the 58 known A alleles.

In the more common case, the patient sample is heterozygotic. The base-called sample appears as a normal sequence of bases with, sporadically, two bases at one site, each with half the peak height. (This result flows from the high degree of similarity shared among all alleles of each HLA gene. Sequence heterozygosity flows from base substitutions). With 58 alleles, over 1700 heterozygote pairs can be arranged. The laborious determination of the which alleles are present in the test sequence can be simplified using computer analysis. A software program called GENELIBRARIAN™ developed by Visible Genetics Inc. rapidly compares the test sequence to a database which includes all possible homozygote and heterozygote combinations of the alleles. The program identifies those stored sequences that are closest matched to the test sequence. The operator can then determine which allelic pair is in the test sample. If no allelic pair shows an exact match, the software allows the operator to review the test sequence to determine if errors in base-calling or other artifacts are interfering with the analysis.

Various patents and printed publications are referred to in this application. These patents and printed publications are incorporated herein by reference as though fully set forth herein.

What is claimed is:

1. A method for determining the allelic type of a classical HLA Class I gene present in a sample comprising the steps of
combining the sample with an amplification reaction mixture comprising a set of amplification primers selected from the group consisting of the following primer sets:
Seq ID Nos 1 and 2;
Seq. ID Nos 3, 4 and 5; and
Seq ID Nos. 6 and 7;
and cycling the resulting mixture to produce an amplification product;
combining the amplification product with a sequencing reaction mixture comprising one or more oligonucleotide sequencing primers which hybridize to conserved regions of the amplification product under suitable conditions to produce sequencing fragments;
evaluating the sequencing fragments to determine the sequence of at least a portion of exon 2 or exon 3 of the gene in the sample; and
comparing the determined sequence with a standard sequence for known alleles to determine the allelic type of the gene in the sample.

2. The method of claim 1, wherein the sequencing primers are selected from among primers having the sequences given by Seq. ID Nos. 8–21.

3. A method for amplifying a highly polymorphic region of exons 2 and 3 of a classical HLA Class I gene present in a sample comprising the steps of
combining the sample with an amplification reaction mixture comprising a set of amplification primers selected from the group consisting of the following primer sets:
Seq ID Nos 1 and 2;
Seq. ID Nos 3, 4 and 5; and
Seq ID Nos. 6 and 7;
and cycling the resulting mixture to produce an amplification product.

4. A method for determining the sequence of a portion of exon 2 or exon 3 of a classical HLA Class I gene present in a sample comprising the steps of
combining the sample with an amplification reaction mixture comprising a set of amplification primers selected from the group consisting of the following primer sets:
Seq ID Nos 1 and 2;
Seq. ID Nos 3, 4 and 5; and
Seq ID Nos. 6 and 7,
and cycling the resulting mixture to produce an amplification product;
combining the amplification product with a sequencing reaction mixture comprising one or more oligonucleotide sequencing primers which hybridize to conserved regions of the amplification product under suitable conditions to produce sequencing fragments; and
evaluating the sequencing fragments to determine the sequence of at least a portion of exon 2 or exon 3 of the classical HLA Class I gene in the sample.

5. The method of claim 4, wherein the sequencing primers are selected from among primers having the sequences given by Seq. ID Nos. 8–21.

6. A kit for amplification of a highly polymorphic portion of exons 2 and 3 of a classical HLA Class I gene comprising, in packaged combination, at least one set of amplification primers selected from the group consisting of the following primer sets:
Seq ID Nos 1 and 2;
Seq. ID Nos 3, 4 and 5; and
Seq ID Nos. 6 and 7.

7. A kit for sequencing of a highly polymorphic portion of exon 2 or 3 of a classical HLA Class I gene comprising, in packaged combination,
at least one set of amplification primers for producing an amplification product from a classical HLA Class I gene, said set being selected from the group consisting of the following primer sets:
Seq ID Nos 1 and 2;
Seq. ID Nos 3, 4 and 5; and
Seq ID Nos. 6 and 7; and
at least one sequencing primer having a sequence that hybridizes to the amplification product under suitable conditions to produce sequencing fragments.

8. The kit according to claim 7, wherein the sequencing primer is selected from among the primers having the sequences given by Seq ID Nos. 8–21.

9. The kit according to claim 8, wherein the sequencing primer is labeled with a detectable label.

* * * * *